(12) United States Patent
Michael

(10) Patent No.: US 8,298,436 B2
(45) Date of Patent: Oct. 30, 2012

(54) FLUOROALKENYL POLY[1,6]GLYCOSIDES

(75) Inventor: Jeffrey D. Michael, Marinette, WI (US)

(73) Assignee: Ansul, Incorporated, Marinette, WI (US)

( * ) Notice: Subject to any disclaimer, the term of this patent is extended or adjusted under 35 U.S.C. 154(b) by 924 days.

(21) Appl. No.: 12/250,742

(22) Filed: Oct. 14, 2008

(65) Prior Publication Data

US 2009/0095936 A1    Apr. 16, 2009

Related U.S. Application Data

(60) Provisional application No. 60/980,323, filed on Oct. 16, 2007.

(51) Int. Cl.
| | |
|---|---|
| A62D 1/00 | (2006.01) |
| A62D 1/08 | (2006.01) |
| C09K 21/08 | (2006.01) |
| A62C 3/00 | (2006.01) |
| A62C 2/00 | (2006.01) |
| C07H 15/10 | (2006.01) |
| C07H 17/04 | (2006.01) |

(52) U.S. Cl. ............... 252/2; 252/8.05; 169/44; 169/45; 169/46; 536/4.1; 536/18.3; 536/18.4; 536/18.5; 536/18.6; 536/120; 536/122; 536/124; 536/127; 510/470

(58) Field of Classification Search .................... 536/4.1, 536/18.3, 18.4, 18.5, 18.6, 120, 12, 124, 536/127, 122; 510/470; 252/2, 8.05; 169/44, 169/45, 46

See application file for complete search history.

(56) References Cited

U.S. PATENT DOCUMENTS

| | | | |
|---|---|---|---|
| 3,219,656 A | 11/1965 | Boettner | |
| 3,258,423 A | 6/1966 | Tuve et al. | |
| 3,547,828 A | 12/1970 | Mansfield et al. | |
| 3,598,865 A | 8/1971 | Lew | |
| 4,510,306 A | 4/1985 | Langdon | |
| 4,536,298 A | 8/1985 | Kamei et al. | |
| 4,713,447 A | 12/1987 | Letton | |
| 4,795,590 A | 1/1989 | Kent et al. | |
| 4,957,904 A | 9/1990 | Falk et al. | |
| 4,985,550 A | 1/1991 | Charpiot et al. | |
| 4,987,225 A | 1/1991 | Pickens | |
| 5,085,786 A | 2/1992 | Alm et al. | |
| 5,218,021 A | 6/1993 | Clark et al. | |
| 5,266,690 A | 11/1993 | McCurry, Jr. et al. | |
| 5,599,476 A * | 2/1997 | Behler et al. | 510/135 |
| 5,616,273 A | 4/1997 | Clark et al. | |
| 5,750,043 A | 5/1998 | Clark | |
| 5,753,606 A * | 5/1998 | Hees et al. | 510/422 |
| 5,783,553 A * | 7/1998 | Desai et al. | 510/470 |
| 5,939,370 A | 8/1999 | Petit et al. | |
| 5,962,399 A | 10/1999 | Wulff et al. | |
| 6,204,369 B1 | 3/2001 | Roth et al. | |
| 7,033,984 B2 * | 4/2006 | Hafkamp et al. | 510/344 |
| 2007/0023740 A1 | 2/2007 | Michael | |
| 2007/0161536 A1 | 7/2007 | Behler et al. | |
| 2009/0082284 A1 * | 3/2009 | Sorns et al. | 514/23 |
| 2011/0039950 A1 * | 2/2011 | Behler et al. | 514/777 |

FOREIGN PATENT DOCUMENTS

| | | |
|---|---|---|
| EP | 0255443 A1 | 2/1988 |
| WO | WO 92/15371 | 9/1992 |

OTHER PUBLICATIONS

Brace, N. O. *J. Fluorine Chem.* 1999, 93, 1-25.
Dolbier, W. R. *Chem. Rev.* 1996, 96, 1557-1584.
Huang, *J. Fluorine Chem.* 1992, 58, 1-8.
Miethchen & Hein, *Tet. Letters* 1998, 39, 6679-6682.
Miethchen & Hein, *Carbohydrate Research* 2000, 327, 169-183.
Riess et al., *J. Med. Chem.* 1990, 33,1262-1269.
Riess et al., *New J. Chem.* 1991, 15, 337-344.
Riess & Greiner, *Carbohydrate Research* 2000, 327, 147-168.
Rollin et al., *Carbohydrate Research* 1999, 318, 171-179.
Talley et al., *J. Am. Chem. Soc.*, 1945, 67, 2037-2039.
Yuasa & Yuasa, *Org. Process Research & Development* 2004, 8, 405-407.
International Search Report—Sep. 30, 2009.

* cited by examiner

*Primary Examiner* — Joseph D Anthony
(74) *Attorney, Agent, or Firm* — Brinks Hofer Gilson & Lione

(57) ABSTRACT

Fire extinguishing compositions and methods of extinguishing a fire comprising compounds of formula (I) where $R^f$ is a fluorocarbon group. The compounds and compositions described herein are useful as intermediates in the preparation of or as additives to AFFF (aqueous film forming foam) formulations used for the extinguishment of fuel and solvent fires.

24 Claims, No Drawings

FLUOROALKENYL POLY[1,6]GLYCOSIDES

RELATED APPLICATIONS

The present patent document claims the benefit of the filing date under 35 U.S.C. §119(e) of Provisional U.S. Patent Application Ser. No. 60/980,323, filed Oct. 16, 2007, which is hereby incorporated by reference.

TECHNICAL FIELD

This disclosure relates to fluorinated compounds, fire extinguishing compositions comprising fluorinated compounds, and to methods for extinguishing, controlling, or preventing fires by using such compositions. It particularly relates to fluoroalkenyl poly[1,6]glycosides.

BACKGROUND

Firefighting foam concentrates are mixtures of foaming agents, solvents and other additives. These concentrates are intended to be mixed with water, the resulting solution foamed by mechanical means, and the foam projected onto the surface of a burning liquid. A particular class of firefighting foam concentrates is known as an aqueous film-forming foam (AFFF). AFFF concentrates have the quality of being able to spread an aqueous film on the surface of hydrocarbon liquids, enhancing the speed of extinguishment of fuel and solvent fires. Surfactants added to AFFF lower surface tension values which permits the foam to spread on the surface of the hydrocarbon liquids.

Aqueous film-forming foams provide a blanket to cover the fuel surface excluding air preventing further ignition of the fuel. For this reason aqueous film-forming foam compositions are particularly desirable for extinguishing fires involving flammable fuels, such as gasoline, naphtha, diesel oils, hydraulic fluids and other hydrocarbons.

Aqueous film-forming foams need a surfactant to impart important film forming properties that are useful in the extinguishment of burning liquids. Alkyl polyglycosides (APG's) are a well known class of non-ionic surfactants. APG's may be prepared by acid catalyzed reaction of fatty alcohols with a mono- or disaccharide (e.g. glucose, galactose, sucrose, maltose, etc.), or a polysaccharide source of these sugars (e.g. starch or corn syrup). A variety of reaction conditions for synthesizing APG's are known using various starting materials and various types of acid catalysts.

Schulz and Flory developed a one-parameter equation to represent the distribution of products in a polymer reaction which is applicable to the linear condensation polymerization of monosaccharides to form di- or polysaccharides. Although it is possible to control the ratio of products to some extent by adjusting the stoichiometry of reactants, the Schulz and Flory equation predicts that the monoglycoside predominates. Typically, the resulting product is composed of around 50 to 70% of the monoglycoside. However, the product also contains decreasing amounts of di-, tri-, tetra-, etc. glycosides, which is referred to as the "Flory distribution" of mono and polyglycosides. (U.S. Pat. No. 5,962,399) Thus, the "Flory distribution" refers to a product mixture of predominantly monoglycoside and decreasing amounts of each higher polyglycoside. For example, the disaccharide would be present in a molar amount less than the monosaccharide, but more than the trisaccharide, etc.

It has been suggested that the polyglycoside portion of the product mixture has superior surfactant properties over the monoglycoside (U.S. Pat. No. 3,598,865), and several methods have been proposed for enriching the polyglycoside portion of the product by removing monoglycoside by solvent extraction (U.S. Pat. Nos. 3,219,656; 3,547,828; and Talley et al., J. Am. Chem. Soc., 1945, 67, 2037-2039 or vacuum distillation (U.S. Pat. No. 5,962,399).

Fluorine analogs of the APG's are also known in which the alkyl chain is partly or completely perfluorinated. These materials have found use as liquid crystals (Miethchen & Hein, *Carbohydrate Research* 2000, 327, 169-183) and biomedical emulsifying agents (Riess & Greiner, *Carbohydrate Research* 2000, 327, 147-168; U.S. Pat. No. 4,985,550).

Among the variety of preparative methods disclosed in these publications are specific procedures for the synthesis of protected mono- and di-glycosides using Koenigs-Knorr (Riess et al., *New J. Chem.* 1991, 15, 337-344) or Mitsunobu chemistry (Rollin et al., *Carbohydrate Research* 1999, 318, 171-179), or by radical addition of perfluoroalkyl iodides to alkenyl glycosides such as allyl glucoside (Miethchen & Hein, *Tet. Letters* 1998, 39, 6679-6682) or pentenyl maltoside (Riess et al., *New J. Chem.* 1991, 15, 337-344).

Radical addition chemistry allows a variety of perfluoroalkyl groups to be added to a common sugar derivative, and a wide variety of such sugar derivatives are accessible using known carbohydrate chemistry. This chemistry generally involves a number of synthetic steps including protection-deprotection of the specific sugar being derivatized (Riess et al., *New J. Chem.* 1991, 15, 337-344; Riess et al., *J. Med. Chem.* 1990, 33, 1262-1269; Huang, *J. Fluorine Chem.* 1992, 58, 1-8; Yuasa & Yuasa, *Org. Process Research & Development* 2004, 8, 405-407). A chemical process for the preparation of perfluoroalkyl thioglycosides for biomedical and surfactant use is also known (U.S. Pat. No. 4,957,904).

What is needed are nonionic fluoroalkyl glycosides which are enriched in the polyglycoside which can enhance the fire extinguishment properties and stability of firefighting foams.

BRIEF SUMMARY

The present invention is directed to alkyl polygylcoside compositions and halogenated derivatives thereof, as well as methods of making these compositions. Preferred compositions are non-ionic surfactants useful in fire retardant compositions, such as foams. Particularly preferred compositions include fluoroalkenyl poly[1,6]glycosides of formula (I), fire extinguishing compositions and methods of extinguishing a fire comprising compounds of formula (I) where $R^f$ is a fluorocarbon group L is an ether, such as (—$CH_2CH_2O$—)$_n$, or (—$CH_2CH(OH)CH_2O$—)$_n$, or L is an alkyl (—$CH_2$—)$_n$; n is integer, preferably 0 to 8; x>1; and $R^f$ is hydrogen or a fluorocarbon group.

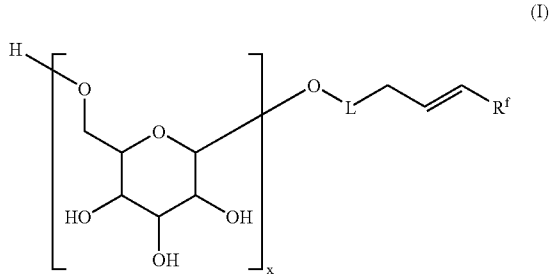

(I)

The compositions may include a ratio of alkyl polyglycoside compounds to monoglycoside compounds that is greater than the corresponding ratio predicted by a Flory distribution of mono- and polyglycoside compounds. Methods of making such compounds with an elevated proportion of alkylpolyglycoside compounds compared to alkyl monoglycoside compounds (compared to the Flory distribution) are also provided. The compounds and compositions described herein are useful, for example, as intermediates in the preparation of or as additives to AFFF (aqueous film forming foam) formulations used for the extinguishment of fuel and solvent fires. These compounds have been discovered to greatly improve the stability of foams used to extinguish fires. The compounds described herein are also useful as intermediates in the preparation of or as liquid crystals and biomedical emulsifying agents, including oxygen carriers.

In a first embodiment, compounds of formula (I) are provided where and L is as defined below, and $R^f$ is hydrogen or a fluorocarbon group, with the proviso that when $R^f$ is hydrogen, n is 1 to 8.

In a second embodiment, a fire extinguishing composition is provided. The composition comprises a solvent and a first fluorosurfactant of formula (I) where L are as defined below, and $R^f$ is a fluorocarbon group. In some aspects, the composition further comprises a hydrocarbon surfactant; and a second fluorosurfactant.

In a third embodiment, a method of extinguishing a fire is provided. the method comprises applying to the fire a composition comprising a solvent and a first fluorosurfactant of formula (I) where $R^1$, $R^2$, $R^3$, and L are as defined below, and $R^f$ is a fluorocarbon group. In some aspects, the composition further comprises a hydrocarbon surfactant; and a second fluorosurfactant.

In a fourth embodiment, a method of making the compounds or compositions of the first and second embodiments, respectively, is provided.

DETAILED DESCRIPTION

The present invention relates to fluoroalkenyl poly[1,6] glycosides, intermediates in the synthesis thereof, including alkenyl poly[1,6]glycosides, and fire extinguishing compositions and methods of extinguishing a fire comprising fluoroalkenyl poly[1,6]glycosides. Fluoroalkenyl poly[1,6]glycosides have been found to be useful additives to AFFF (aqueous film forming foam) formulations used for the extinguishment of fuel and solvent fires. These compounds are a type of nonionic fluorosurfactant and as such provide the useful properties of low surface tension, aqueous film formation, and fuel vapor suppression. In addition, these compounds have been discovered to greatly improve the stability of foams generated from ionic hydrocarbon and fluorocarbon surfactants. Without wishing to be bound by theory, the polyglycosides are believed to be responsible for this property. Pure perfluoroalkenyl monoglycosides have been found to provide very feeble foam generation and do not enhance the foam quality of other foam producing surfactants in the formulation.

Abbreviations and Definitions

When describing the compounds, compositions, methods and processes of this invention, the following terms have the following meanings, unless otherwise indicated.

"Alkyl" by itself or as part of another substituent refers to a hydrocarbon group which may be linear, cyclic, or branched or a combination thereof having the number of carbon atoms designated (i.e., $C_{1-8}$ means one to eight carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. Alkyl groups can be substituted or unsubstituted, unless otherwise indicated. Examples of substituted alkyl include haloalkyl, thioalkyl, aminoalkyl, and the like.

"Alkenyl" refers to an unsaturated hydrocarbon group which may be linear, cyclic or branched or a combination thereof. Examples of alkenyl groups include ethenyl, allyl, n-propenyl, isopropenyl, n-but-2-enyl, n-hex-3-enyl, cyclohexenyl, cyclopentenyl and the like. Alkenyl groups can be substituted or unsubstituted, unless otherwise indicated. Preferred alkenyl groups comprise a terminal alkene.

"Alkynyl" refers to an unsaturated hydrocarbon group which may be linear, cyclic or branched or a combination thereof. The alkynyl group may contain 1, 2 or 3 carbon-carbon triple bonds. Examples of alkynyl groups include ethynyl, n-propynyl, n-but-2-ynyl, n-hex-3-ynyl and the like. Alkynyl groups can be substituted or unsubstituted, unless otherwise indicated.

"Fluoroalkyl" and "fluorocarbon" as used herein are interchangeable. As a substituted alkyl group, "fluoroalkyl" and "fluorocarbon" refer to an alkyl group having one or more hydrogen atoms along the carbon skeleton of the alkyl chain replaced by a fluorine atom, wherein enough fluorine is incorporated for the poly[1,6]glycosides comprising the fluoroalkyl group to have fire extinguishing properties. An example of a fluoroalkyl group is a monovalent fluoroalkyl group of formula $C_mH_{(2m+1-x)}F_x$. The variable "m" is an integer from 1 to 20, preferably from 4 to 10, more preferably 6. The variable "x" is an integer greater than 0 and less than or equal to 2m+1, preferably at least m, more preferably 2m+1. When 2m+1 is equal to x, the monovalent fluoroalkyl group is a perfluoroalkyl group. In other words, a perfluoro group has a carbon skeleton that is 100% fluorinated, including for example —$CF_2CF_2CF_2CF_2CF_2CF_3$, —$C_{10}F_{21}$, and the like. Fluoroalkyl groups may be straight chain or branched chains, but preferably are straight chain.

"Carbon skeleton" as used herein refers to a carbon chain which may be linear, cyclic, or branched or a combination thereof. The carbon skeleton may have the number of carbon atoms designated (i.e., $C_{1-8}$ means one to eight carbon atoms).

"Glycoside" as used herein refers to any molecule where a sugar group is bonded through its anomeric carbon to a nonsugar group by an oxygen. This is called a glycosidic bond.

"Sugar" as used herein is interchangeable with carbohydrate or saccharide and refers to molecules that are straight-chain aldehydes or ketones with hydroxyl groups added and optionally substituted or unsubstituted amino groups added. Preferably, the straight-chain aldehyde or ketone has one hydroxyl group on each carbon atom that is not part of the aldehyde or ketone functional group. The straight-chain aldehyde or ketone may form or be in equilibrium with cyclic ring forms, including, for example pentoses or hexoses, wherein one of the hydroxyl oxygens reacts with the aldehyde or ketone carbon to form an oxygen containing ring such as a tetrahydrofuran or tetrahydropyran. The basic carbohydrate units are called monosaccharides, such as glucose, galactose, and fructose. The general chemical formula of an unmodified monosaccharide is $(CH_2O)_n$, where n is any number of three or greater. Monosaccharides can be linked together in almost limitless ways. Two joined monosaccharides are called disaccharides, such as sucrose and lactose.

"Polyglycoside" as used herein refers to a glycoside which comprises more than one sugar group.

An "alkenyl alcohol" refers to a molecule with an unsaturated hydrocarbon group which may be used to introduce the alkenyl group of an alkenyl glycoside. Preferably the alkenyl alcohol comprises a terminal alkene.

An "alkenyl glycoside" refers to a glycoside comprising one or more sugars and a nonsugar group comprising an unsaturated hydrocarbon group, preferably a terminal alkene.

An "alkenyl monoglycoside" refers to a glycoside comprising one sugar and a nonsugar group comprising an unsaturated hydrocarbon group, preferably a terminal alkene.

An "alkenyl poly[1,6]glycoside" refers to a glycoside with more than one sugar group, wherein the sugar groups are linked via oxygen atoms attached to the 1 and 6 carbons of the sugar, and the nonsugar group comprises an unsaturated hydrocarbon group, preferably a terminal alkene.

A "fluoroalkylating agent" refers to a molecule capable of forming a fluoroalkyl radical.

A "fluoroalkenyl poly[1,6]glycoside: refers to a glycoside with more than one sugar group, wherein the sugar groups are linked via oxygen atoms attached to the 1 and 6 carbons of the sugar, and the nonsugar group comprises fluoroalkyl group.

As used herein, "glycol" refers to a compound comprising two hydroxyl groups. The hydroxyl groups may be geminal, vicinal, or further spaced along a carbon skeleton. Examples of glycol include, but are not limited to ethylene glycol, propylene glycol, 1,4-butanediol and the like.

The term "organic acid" refers to a carbon-containing product which is capable of donating a proton.

Certain compounds of the present invention can exist in unsolvated forms as well as solvated forms, including hydrated forms. In general, both solvated forms and unsolvated forms are intended to be encompassed within the scope of the present invention. Certain compounds of the present invention may exist in multiple crystalline or amorphous forms (i.e., as polymorphs). In general, all physical forms are equivalent for the uses contemplated by the present invention and are intended to be within the scope of the present invention.

It will be apparent to one skilled in the art that certain compounds of the present invention may exist in tautomeric forms, all such tautomeric forms of the compounds being within the scope of the invention. Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Compounds

In one embodiment, compounds of formula (I) are provided:

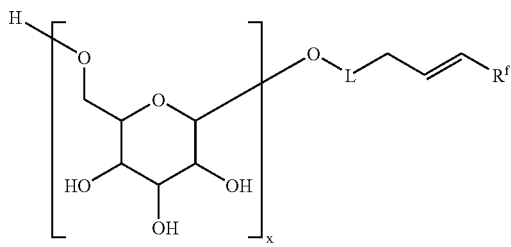

(I)

where
L is $(—CH_2CH_2—)_n$, $(—CH_2CH(OH)CH_2O—)_n$, or $(—CH_2—)_n$;
n is 0 to 8;
x>1; and
$R^f$ is hydrogen or a fluorocarbon group. In one aspect, compounds of formula (I) are provided with the proviso that when $R^f$ is hydrogen, n is 1 to 8.

In another embodiment, compounds of formula (II) are provided:

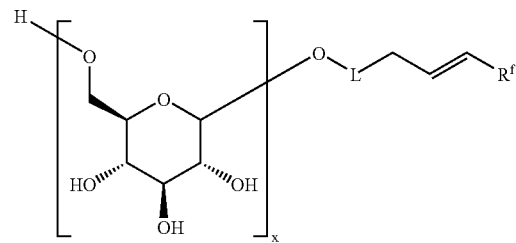

(II)

where
L, n, x, and $R^f$ are as defined for formula (I);
with the proviso that when $R^f$ is hydrogen, n is 1 to 8.
In one embodiment of formulae (I or II), $R^f$ is hydrogen.
In one embodiment of formulae (I or II), $R^f$ is a fluorocarbon group.
In one embodiment of formulae (I or II), $R^f$ is a perfluoroalkyl group.
In one embodiment of formulae (I or II), $R^f$ is a perfluoroalkyl group having a $C_1$-$C_{20}$ carbon skeleton.
In one embodiment of formulae (I or II), $R^f$ is a perfluoroalkyl group having a $C_4$-$C_{10}$ carbon skeleton.
In one embodiment of formulae (I or II), $R^f$ is a perfluoroalkyl group having a $C_6$ carbon skeleton.
In one embodiment of formulae (I or II), n is 1.
In one embodiment of formulae (I or II), n is 0 and $R^f$ is a fluorocarbon group.
In one embodiment of formulae (I or II), n is 0, and $R^f$ is a perfluoroalkyl group.
In one embodiment of formulae (I or II), L is $—CH_2CH_2O—$.
In one embodiment of formulae (I or II), L is $(—CH_2CH_2O—)_n$.
In one embodiment of formulae (I or II), L is $(—CH_2CH(OH)CH_2O—)_n$.
In one embodiment of formulae (I or II), L is $(—CH_2CH(OH)CH_2O—)$.
In one embodiment of formulae (I or II), L is $(—CH_2—)_n$.
In one embodiment of formulae (I or II), L is $(—CH_2—)$.
In one embodiment of formulae (I or II), L is $(—CH_2CH_2O—)$, $(—CH_2CH(OH)CH_2O—)$, or $(—CH_2—)$.
In one embodiment of formulae (I or II), x>2.
In one embodiment of formulae (I or II), x>3.
In one embodiment of formula (I), L is $(—CH_2CH_2O—)_n$; n is 1 to 8; x>1; and $R^f$ is a perfluoroalkyl group having a $C_4$-$C_{10}$ carbon skeleton.
In one embodiment of formula (I), L is $(—CH_2CH_2O—)_n$; n is 1 to 8; x>1; and $R^f$ is a perfluoroalkyl group having a $C_6$ carbon skeleton.
In one embodiment of formula (I), L is $(—CH_2—)_n$; n is 1 to 8; x>1; and $R^f$ is a perfluoroalkyl group having a $C_4$-$C_{10}$ carbon skeleton.

In one embodiment of formula (I), L is (—CH$_2$—)$_n$; n is 1 to 8; x>1; and R$^f$ is a perfluoroalkyl group having a C$_6$ carbon skeleton.

In one embodiment of formula (I), L is (—CH$_2$CH(OH)CH$_2$O—)$_n$; n is 1 to 8; x>1; and R$^f$ is a perfluoroalkyl group having a C$_4$-C$_{10}$ carbon skeleton.

In one embodiment of formula (I), L is (—CH$_2$CH(OH)CH$_2$O—)$_n$; n is 1 to 8; x>1; and R$^f$ is a perfluoroalkyl group having a C$_6$ carbon skeleton.

In one embodiment of formula (I), L is (—CH$_2$CH$_2$O—)$_n$; n is 1 to 8; x>1; and R$^f$ is hydrogen.

In one embodiment of formula (I), L is (—CH$_2$—)$_n$; n is 1 to 8; x>1; and R$^f$ is hydrogen.

In one embodiment of formula (I), L is (—CH$_2$CH(OH)CH$_2$O—)$_n$; n is 1 to 8; x>1; and R$^f$ is hydrogen.

Compositions

In one embodiment, fire extinguishing compositions are provided. The compositions comprise a solvent, and a compound of formula (I) where L is (—CH$_2$CH$_2$O—)$_n$, (—CH$_2$CH(OH)CH$_2$O—)$_n$, or (—CH$_2$—)$_n$; n is 0 to 8; x>1; and R$^f$ is a fluorocarbon group.

The term "composition" as used herein is intended to encompass a product comprising the specified ingredients in the specified amounts, as well as any product which results, directly or indirectly, from combination of the specified ingredients in the specified amounts.

The compositions may be foams, including AFFF (aqueous film forming foam) formulations or concentrates used for the extinguishment of fuel and solvent fires. Concentrates upon dilution with water and aeration, produce a foam. The compositions comprise fluoroalkenyl poly[1,6]glycosides of formula (I). Fluoroalkenyl polyglycosides improve the stability of foams, whereas fluoroalkenyl monoglycosides are feeble foam generators.

Preferably, the compositions include a polyglycoside component. More preferably, the compositions include an amount of polyglycoside effective to provide desired surfactant properties to the composition. In one example, the composition includes an amount of one or more alkyl polyglycosides or fluorinated derivates thereof that are greater than the amount provided by a Flory distribution. In another aspect, the composition includes a ratio of a polyglycoside compound (or a fluorinated alkyl derivative thereof, such as a compound of formula (I)) to a corresponding monoglycoside compound that is greater than the ratio provided by the Flory distribution. Schulz and Flory developed a one-parameter equation to represent the distribution of products in a polymer reaction which is applicable to the linear condensation polymerization of monosaccharides to form di- or polysaccharides. Although it is possible to control the ratio of products to some extent by adjusting the stoichiometry of reactants, the Schulz and Flory equation predicts that the monoglycoside predominates. Typically, the resulting product is composed of around 50 to 70% of the monoglycoside. However, the product also contains decreasing amounts of di-, tri-, tetra-, etc. glycosides, which is referred to as the "Flory distribution" of mono and polyglycosides. Thus, the "Flory distribution" refers to a product mixture of predominantly monoglycoside and decreasing amounts of each higher polyglycoside. For example, the disaccharide would be present in a molar amount less than the monosaccharide, but more than the trisaccharide, etc. Therefore, the preferred compositions may include less than the amount of a monoglycoside product of an optionally fluorinated glycoside compound, such as a fluoroalkenyl[1,6]glycoside. Preferably, the composition contains less than about 70 mole %, 60 mole %, or 50 mole % mono fluoroalkenyl[1,6]glycoside, and most preferably less than 50 mole %, 40 mole %, 30 mole %, 25 mole %, 20 mole %, 15 mole %, 10 mole %, 5 mole % or 1 mole %.

In another aspect, the composition may be a fire extinguishing composition comprising a non-Flory distribution of fluoroalkenyl glycosides which is enriched in the polyglycoside components. The compositions comprise a fluoroalkenyl [1,6]glycoside with less than about 50 mole %, more preferably less than about 25 mole % of the monoglycoside, most preferably less than about 10 mole %, even more preferably less than about 1 mole %, wherein the monoglycoside mole % is relative to the entire glycoside content of the composition.

The compositions may be provided in the form of solutions, dispersions, gels, emulsions and microemulsions in a solvent. The solvent is water, a water miscible solvent, or combination thereof. Water miscible solvents include, for example, alcohols (for example, ethanol, propanol, iso-propyl alcohol, t-butyl alcohol); glycols (for example, ethylene glycol, propylene glycol, 1,4-butanediol); and glycol derivatives (for example butyl carbitol also known as diethylene glycol monobutyl ether, and dipropylene glycol monobutyl ethe)r. Preferable solvents are water, iso-propyl alcohol, t-butyl alcohol, and ethylene glycol.

In some aspects, the composition may comprise a hydrocarbon surfactant. The term hydrocarbon surfactants as used herein refers to surfactants which are non-fluorinated surfactants and comprise a hydrophobic group and hydrophilic group. Hydrocarbon surfactants may be ionic (anionic, cationic, amphoteric) or nonionic. Hydrocarbon surfactants are known to one skilled in the art, including but not limited to those disclosed in U.S. Pat. Nos. 4,795,590; 3,772,195; 5,207,932; 6,436,306. Any suitable hydrocarbon surfactant known to one skilled in the art may be used in the compositions. Amphoteric hydrocarbon surfactants include those comprising amino and carboxy groups, and those comprising amino and sulfo groups. Nonionic hydrocarbon surfactants include polyoxyethylene derivatives of alkyl phenols, linear or branched alcohols, fatty acids, alkyl polyglycosides, and block copolymers containing polyoxyethylene and polyoxypropylene units. Other examples of hydrocarbon surfactants include for example, sodium laureth sulfate, also known as sodium lauryl ether sulfate (SLES); polyoxyethylene ether alcohol; dioctyl sodium sulfosuccinate; ammonium alkyl phenoxy polyoxyethylene sulfate; alkyl ether sulfate surfactants In other aspects, the composition may comprise another fluorosurfactant in addition to the compounds described above, such as the fluoroalkenyl poly[1,6]glycoside of formula (I). The term fluorosurfactants as used herein refers to surfactants which are fluorinated and comprise a hydrophobic group and hydrophilic group. Fluorosurfactants may be ionic (anionic, cationic, amphoteric) or nonionic. Fluorosurfactants are known to one skilled in the art, including but not limited to those disclosed in U.S. Pat. Nos. 3,258,423; 4,536,298; 4,795,590; and 5,085,786. In other aspects, the composition may comprise a fluorocarbon polymer. Fluorocarbon polymers are known to one skilled in the art and include, but are not limited to, those disclosed in U.S. Pat. Nos. 5,616,273; 5,750,043, and 5,218,021. In other aspects, the composition may comprise a first fluorosurfactant of formula (I), a hydrocarbon surfactant, and a second fluorosurfactant.

The compositions may also comprise additives, including inorganic salts, generally in the form of buffers, which allow the pH to be adjusted to a suitable range.

Process for Preparing poly[1,6]glycoside

In another aspect, the present invention provides a process for preparing a composition described above, such as a poly [1,6]glycoside. The process may comprise the steps of providing a sugar; providing an alkenyl alcohol; combining the sugar and the alkenyl alcohol; reacting the sugar with the alkenyl alcohol; isolating an alkenyl polyglycoside mixture; and purifying the alkenyl polyglycoside mixture to afford a product, such as an alkenyl poly[1,6]glycoside in solid form.

An "alkenyl alcohol" refers to a molecule with an unsaturated hydrocarbon group which may be used to introduce the alkenyl group of an alkenyl glycoside. The alkenyl alcohol comprises a terminal alkene.

In some aspects of the present invention, the alkenyl alcohol is of formula (III):

(III)

where
L is $(-CH_2CH_2O-)_n$, $(-CH_2CH(OH)CH_2O-)_n$, or $(-CH_2-)_n$; and
n is 0 to 8.

The term "sugar" refers to molecules that are straight-chain aldehydes or ketones with hydroxyl groups added and optionally substituted or unsubstituted amino groups added. Preferably, the straight-chain aldehyde or ketone has one hydroxyl group on each carbon atom that is not part of the aldehyde or ketone functional group. The straight-chain aldehyde or ketone may form or be in equilibrium with cyclic ring forms, including, for example pentoses or hexoses, wherein one of the hydroxyl oxygens reacts with the aldehyde or ketone carbon to form an oxygen containing ring such as a tetrahydrofuran or tetrahydropyran. The sugar may be a monosaccharide, including for example glucose, galactose, and fructose.

In other aspects the sugar may comprise more than one monosaccharide. Two joined monosaccharides are called disaccharides, such as sucrose and lactose. Polysaccharides, as used herein, refers compounds formed by joining two or more monosaccharides. Monosaccharides can be linked together in almost limitless ways to form polysaccharides. When a polysaccharide is used as the sugar in the process of the present invention, the polysaccharide may or may not comprise the [1,6]glycosidic linkage. Preferably, when a polysaccharide is used as the sugar in the process of the present invention, the polysaccharide comprises the natural [1,4]glycosidic linkage.

Preferable sugars include corn syrup, starch, cellulose, glucose or maltose, more preferably glucose.

The process of the present invention comprises combining and reacting the sugar and the alkenyl alcohol. Combining the sugar and alkenyl alcohol may be done under any suitable conditions. The sugar and alkenyl alcohol may be combined neat or in the presence of a solvent, for example. The combining of the sugar and alkenyl alcohol may form a solution, a suspension, solid, oil, and the like. Reacting the sugar and alkenyl alcohol may be performed under any suitable conditions known to one skilled in the art to form an ether bond between the sugar and alkenyl alcohol, more specifically an ether bond between the alcohol oxygen and anomeric carbon of the sugar. Suitable conditions include, for example, acid catalysis. When acid catalysis is employed the acid may be a Lewis acid including Brønsted-Lowry acids, mineral acids, and organic acids. Preferably an organic acid is employed, more preferably para-toluenesulfonic acid.

The reacting of the sugar and alkenyl alcohol is performed under conditions which minimize the presence of water. Anhydrous sugar, alkenyl alcohol or acid catalyst may be employed to minimize the presence of water. Water may be removed from the reaction mixture during the reacting of the sugar with the alkenyl alcohol by a Barrett style water separator or Dean-Stark trap, for example.

The process further comprises isolating an alkenyl polyglycoside mixture. Isolating the alkenyl polyglycoside mixture may be performed by any suitable conditions known to one skilled in the art including for example solvent extraction, distillation, precipitation, or adsorption. Preferably, distillation conditions are employed in which the alkenyl monoglycoside is volatilized by the addition of heat either at atmospheric or reduced pressure conditions. In this aspect, alkenyl monoglycoside is removed via distillation, leaving the alkenyl polyglycoside mixture.

The alkenyl polyglycoside mixture comprises a mixture of alkenyl glycosides, the major component being alkenyl poly[1,6]glycosides, including for example alkenyl di[1,6]glycoside, alkenyl tri[1,6]glycoside, alkenyl tetra[1,6]glycoside, and the like. The monoglycoside is a minor component of the mixture, comprising less than 25% by wt. of the alkenyl polyglycoside mixture, preferably less than 10%, more preferably less than 5%, most preferably less than 1%.

In another aspect of the present invention, the alkenyl polyglycoside mixture may be represented by formula (V):

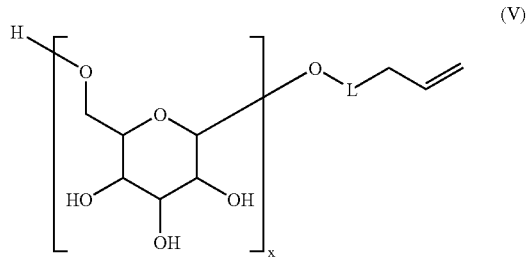
(V)

where x is >0 and L is as defined for formula (I).

In another aspect of the present invention, the alkenyl polyglycoside mixture may be represented by formula (VI):

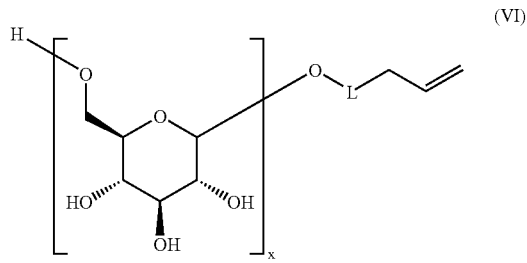
(VI)

where x is >0 and L is as defined for formula (I).

The process further comprises purifying the alkenyl polyglycoside mixture to afford alkenyl poly[1,6]glycoside in solid form. Solid form includes crystalline, amorphous, semi-solid forms, or any other partially solid form. Purifying the alkenyl polyglycoside mixture may be performed by any suitable conditions known to one skilled in the art including for example solvent extraction, distillation, precipitation, or adsorption. Preferably, precipitation conditions are used for purifying the alkenyl polyglycoside mixture. The alkenyl poly[1,6]glycoside is at least 90% pure by weight, preferably 95%, more preferably 98%, most preferably 99% pure. The alkenyl poly[1,6]glycoside comprises less than about 5 wt % alkenyl monoglycoside, preferably less than 1 wt %, more preferably less than 0.5 wt %.

In other embodiments of the present invention, the process further comprises removing water during the reacting of the sugar with the alkenyl alcohol; precipitating the alkenyl polyglycoside mixture; precipitating the alkenyl poly[1,6]glycoside; and wherein the reacting is done in the presence of an organic acid.

In other embodiments of the present invention, the process further comprises providing a fluoroalkylating agent; combining the alkenyl poly[1,6]glycoside and the fluoroalkylating agent in the presence of a radical initiator; and forming a fluoroalkenyl poly[1,6]glycoside.

A "fluoroalkylating agent" refers to a molecule capable of forming a fluoroalkyl radical. For example, the fluoroalkylating agent may be a fluoroalkyl halide, preferably a fluoroalkyl iodide. The fluoroalkyl portion of the fluoroalkylating agent refers to a partially fluorinated or perfluoroalkyl group. Preferably the fluoroalkylating agent is a perfluoroalkyl halide, more preferably, a perfluoroalkyl iodide. The perfluoroalkyl portion of the fluoroalkylating agent may be straight chain or branched, preferably straight chain. The length of the chain may be $C_{1-20}$, preferably $C_{4-10}$, more preferably $C_6$.

Combining the alkenyl poly[1,6]glycoside and the fluoroalkylating agent may be done under any suitable conditions. The alkenyl poly[1,6]glycoside and the fluoroalkylating agent may be combined neat or in the presence of a solvent, for example. The combining of the alkenyl poly[1,6]glycoside and the fluoroalkylating agent may form a solution, a suspension, solid, oil, and the like Any suitable radical initiators known to one skilled in the art may be employed including chemical, UV, and heat initiators and methods disclosed in Dolbier, W. R. *Chem. Rev.* 1996, 96, 1557-1584, and Brace, N. O. *J. Fluorine Chem.* 1999, 93, 1-25. Examples of chemical initiators include, for example, azo initiators such as AIBN (azo-isobutyronitrile), hydroxymethanesulfinic acid sodium salt ($HOCH_2SO_2Na$—also called "Rongalite", sodium dithionite ($Na_2S_2O_4$), thiourea dioxide (($NH_2)_2CSO_2$), metals (Fe, Cu, Zn, etc.) and metal salts such as CuCl/ethanolamine. Preferably the radical initiator is a chemical initiator, more preferably, an azo initiator or hydroxymethanesulfinic acid sodium salt, and most preferably AIBN or hydroxymethanesulfinic acid sodium salt. The radical initiator is present in an amount sufficient to initiate the radical reaction between the fluoroalkylating agent and the alkenyl poly[1,6]glycoside, preferably 10 mole % relative to the fluoroalkyl iodide, more preferably 5 mole %, most preferably 1 mole %.

Forming the fluoroalkenyl poly[1,6]glycoside may done directly, or the intermediate iodide product may be isolated and subjected to dehydroiodination conditions known to one skilled the art to form the fluoroalkenyl poly[1,6]glycoside. The fluoroalkenyl poly[1,6]glycoside formed may be 90% pure by weight, preferably 95% pure, more preferably 99% pure.

In some aspects the fluoroalkenyl poly[1,6]glycoside is of formula (I):

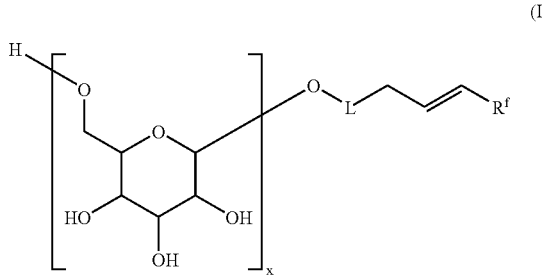

(I)

where L is ($-CH_2CH_2O-$)$_n$, ($-CH_2CH(OH)CH_2O-$)$_n$, or ($-CH_2-$)$_n$; n is 0 to 8; x>1; and $R^f$ is a fluorocarbon group.

In other aspects, the fluoroalkenyl poly[1,6]glycoside is of formula (II):

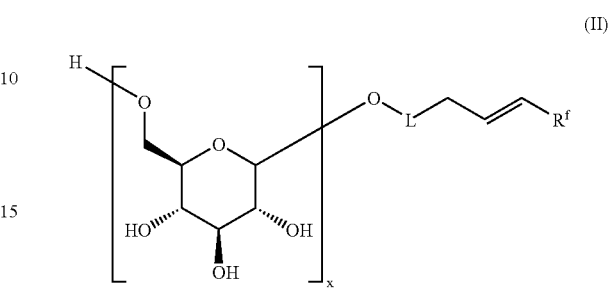

(II)

where L is ($-CH_2CH_2O-$)$_n$, ($-CH_2CH(OH)CH_2O-$)$_n$, or ($-CH_2-$)$_n$; n is 0 to 8; x>1; and $R^f$ a fluorocarbon group.

Method of Extinguishing Fire

In one embodiment, a method of extinguishing a fire is provided. The method comprises applying to a fire a composition comprising a compound of formula (I) where L is ($-CH_2CH_2O-$)$_n$, ($-CH_2CH(OH)CH_2O-$)$_n$, or ($-CH_2-$)$_n$; n is 0 to 8; x>1; and $R^f$ is a fluorocarbon group. The compositions may be a foam, or a concentrate which upon dilution with water and aeration, produces a foam.

The foam or concentrate, upon dilution with water and aeration, produces an aqueous film-forming foam which is applied to a body of flammable liquid such as a spill or pool which is burning or subject to ignition. The foam extinguishes the burning liquid, prevents ignition. The foam provides a blanket to cover the fuel surface excluding air, and preventing further ignition of the liquid. Film-forming foam compositions are particularly desirable for extinguishing fires involving flammable fuels, such as gasoline, naphtha, diesel oils, hydraulic fluids, petroleum and other hydrocarbons. Film-forming foam compositions may also modified to be suitable for extinguishing fires involving polar solvent (including acetone, ethanol, and the like) by methods known to one skilled in the art, including those disclosed in U.S. Pat. Nos. 4,536,298 and 5,218,021.

The concentrates which when diluted with water and aerated produce a low density air-foam which quickly spreads on the surface of a body of hydrocarbon fuel, or other flammable liquid forming a blanket over the fuel or liquid. As the foam (on the surface of the flammable liquid) drains, a film is formed which, if disturbed or broken, tends to reform to seal off hot vapor emanating from the flammable liquid, thus extinguishing the fire. Although hydrocarbon surfactants may form a foam blanket, the flammable liquid vapors may wick through the foam and reignite. Foams comprising fluorosurfactants reduce the ability of the flammable liquid from wicking through the film and thereby prevent reignition.

As water under pressure passes through a fire hose, typically 3 percent by volume of the concentrate composition is inducted into the hose line by venturi effect to form a remixture (or "premix") of the concentrate diluted with water. The premix becomes aerated to produce a foam by use of an air-aspirating nozzle located at the outlet end of the hose. Additional equipment which can be used to produce and apply the aqueous air-foam of the invention is known to one skilled in the art or can be found in publications by the National Fire Protection Association.

In some aspects, the composition is a concentrate, which upon dilution with water and aeration, produces an aqueous film-forming foam. The method of extinguishing a fire may further comprise mixing the concentrate with water passing through a fire extinguishing hose in order to form a premixture; aerating the premixture as it passes through a hose or a nozzle attached thereto to produce an aqueous film-forming foam; and applying the aqueous film-forming foam to a fire, preferably a flammable liquid fire.

The composition can preferably be used in either the gaseous or the liquid state (or both), and any of the known techniques for introducing the composition to a fire can be utilized. For example, a composition can be introduced by streaming, by misting, or by flooding the composition onto a fire or hazard. The composition can optionally be combined with inert propellants, including, for example, nitrogen, argon, or carbon dioxide, to increase the rate of discharge of the composition from the streaming or flooding equipment utilized.

Preferably, the compositions are introduced into a fire or flame in an amount sufficient to extinguish the fire or flame. One skilled in the art will recognize that the amount of extinguishing composition needed to extinguish a particular hazard will depend upon the nature and extent of the hazard.

EXAMPLES

The following examples are offered to illustrate, but not to limit, the claimed invention.

Additionally, those skilled in the art will recognize that the molecules claimed in this patent may be synthesized using a variety of standard organic chemistry transformations.

Certain molecules claimed in this patent can exist in different enantiomeric and diastereomeric forms and all such variants of these compounds are within the scope of the invention.

In the descriptions of the syntheses that follow, some precursors were obtained from commercial sources. These commercial sources include Aldrich Chemical Co.

Compounds of the invention can be made by the methods and approaches described in the following experimental section, and by the use of standard organic chemistry transformations that are well known to those skilled in the art.

The above compounds and others within the scope of this invention can be made and tested for activity using the following procedures.

Reagents and solvents used below can be obtained from commercial sources such as Aldrich Chemical Co. (Milwaukee, Wis., USA.

General Procedure A: Alkenyl Glycosides (Flory Distribution)

D-glucose (180 grams, 1.0 mole) is suspended in the alkenyl alcohol (3.0 moles). p-Toluene sulfonic acid (1.9 gram, 10 mmoles) and hexane (50 mL) are added, and the mixture heated to reflux with good mechanical stirring under a nitrogen atmosphere. The refluxing hexane is returned to the reaction vessel through a Barrett style water separator, and the temperature in the reaction vessel is maintained within a range of about 95-105° C. by adding or removing small amounts of hexane through the Barrett separator. Reflux is continued until no more water is seen collecting in the separator (about 3 to 5 hours). With lower boiling alcohols (such as allyl alcohol) the water collected in the separator will contain a high proportion of the alcohol and will therefore have a higher than theoretical volume (18 mL).

At the end of the reaction period a clear, light amber solution is formed. This is cooled to ambient temperature and made basic by adding 0.44 gram (11 mmoles) of NaOH dissolved in 1 mL of water. The resulting solution comprises a Flory distribution of mono- and polyglycosides and may be used directly in General Procedure B.

General Procedure B: Alkenyl (Poly)glycosides

The product mixture from General Procedure A having a Flory distribution of mono- and polyglycosides (a light syrup) is poured slowly into 1.5 L of rapidly stirred acetone to precipitate a crude mixture of solid polyglycosides. The solid is allowed to settle, and the acetone layer containing most of the monoglycoside and excess alcohol is separated. The acetone wash may be repeated until the solid is essentially free of alcohol and monoglycoside. This is conveniently monitored by TLC (silica gel G; ethyl acetate/methanol 1:1; iodide stain) since the alcohol and monoglycoside are easily resolved from the more polar polyglycosides.

At this stage the polyglycoside product is in the form of a hygroscopic, granular powder or a gummy mass—depending on the alcohol used and the residual moisture content. After removing the last traces of solvent (such as by decanting or filtering), the solid is quickly transferred to a vacuum drying system in order to minimize moisture absorption.

Example 1

1-Allyloxy poly[1,6]glucoside (1)

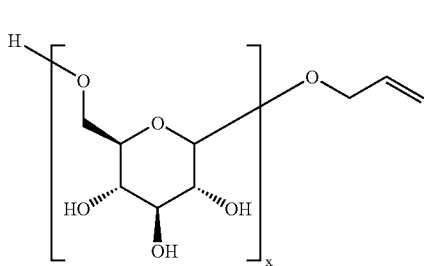

1-Allyloxy polyglucoside is prepared according to general procedure A using allyl alcohol as the alkenyl alcohol and isolated according to general procedure B. The acetone precipitation gave around 120 grams of crude product as a gummy solid, which was converted to a granular solid by dissolving in a small amount of methanol and re-precipitating with acetone. The granular material is stable if protected from moisture.

Example 2

Isolation of 1-Allyloxy monoglucoside (2)

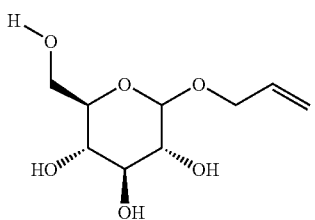

The acetone mother liquors and filtrates from the isolation of 1 above containing excess allyl alcohol and monoglucoside, was evaporated under vacuum to remove acetone and alcohol. The residual solid, 113 grams, consists mainly of monoglucoside (α and β anomers). Column chromatography of a small sample (silica gel; ethyl acetate/methanol 2:1) gave material pure enough to crystallize spontaneously on cooling. Seeding the bulk of the crude monoglucoside in acetone gave 86 grams of crude crystalline α-allyl glucoside. One recrystallization from acetone gave material melting at 94-98° C. (lit. 85-90° and 100.5-101.5° C. (see Talley et al., *J. Am. Chem. Soc.* 67, 2037 (1945)). $^1$H NMR (CD$_3$OD): 5.98 (C═CH—, 1H, m); 5.34-5.17 (CH$_2$═C, 2H, dd); 4.82 (C1 sugar, 1H); 4.04-4.23 (═C—CH$_2$—O, 2H, dd); 3.80-3.28 (C2-6 sugar protons, 6H).

Example 3

1-Allyloxyethoxy poly[1,6]glucoside (3)

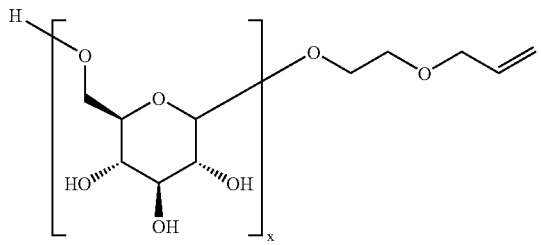

1-Allyloxyethoxy polyglucoside is prepared according to general procedure A using allyloxyethanol as the alkenyl alcohol and isolated according to general procedure B. Acetone precipitation gave 110 grams of beige powder after filtering (dry conditions) and vacuum drying. $^1$H NMR (CD$_3$OD): 5.93 (C═CH—, 1H, m); 5.30-5.17 (CH$_2$═C, 2H, dd); 4.04 (═C—CH$_2$—O,2H, dd); 3.9-3.2 (CH$_2$—CH$_2$ and sugar protons, not integrated).

Example 4

1-Allyloxyethoxy monoglucoside (4)

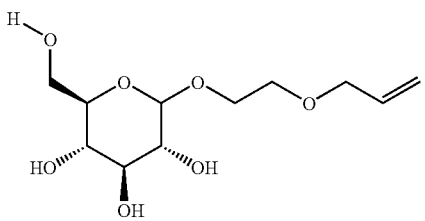

The acetone mother liquors and filtrates from example 3 were evaporated under vacuum and gave 304 grams of syrup consisting mainly of the excess alcohol and monoglucoside. A small sample of the monoglucoside was purified by chromatography as described in example 2, giving 1-allyloxyethoxy glucoside as a clear colorless resin. $^1$H NMR (CD$_3$OD): 5.92 (C═CH—, 1H, m); 5.30-5.18 (CH$_2$═C, 2H, dd); 4.82 (C1 anomeric H, 1H); 4.04 (═C—CH$_2$—O,2H, d); 3.86-3.2 (CH$_2$—CH$_2$ and C2-6 sugar protons, 10H).

Example 5

1-(3-Allyloxy-2-hydroxypropoxy)poly[1,6]glucoside (5)

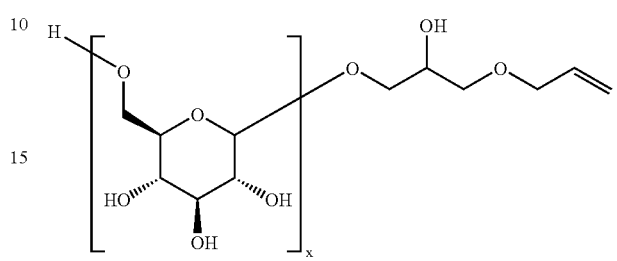

2-(3-Allyloxy-2-hydroxypropyl)polyglucoside is prepared according to general procedure A using 3-allyloxy-2-hydroxypropanol as the alkenyl alcohol and isolated according to general procedure B, except that ethyl acetate is used in place of acetone. Ethyl acetate precipitation gave a gummy solid which was vacuum dried to afford 1-(3-Allyloxy-2-hydroxypropoxy)poly[1,6]glucoside as a white solid foam (124 grams).

Example 6

1-(3-Allyloxy-2-hydroxypropoxy)monoglucoside (6)

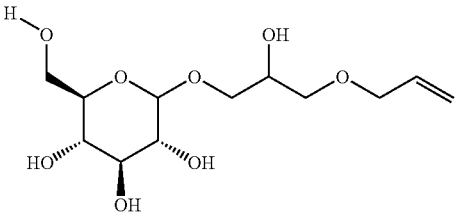

Evaporation of the ethyl acetate mother liquors and filtrates from example 5 gave 341 grams of syrup consisting of the excess alcohol and monoglucoside. Chromatography of a small sample as described in example 2 gave 3-allyloxy-2-hydroxypropyl monoglucoside as a clear oil. $^1$H NMR (CD$_3$OD): 5.92 (C═CH—, 1H, m); 5.28-5.16 (CH$_2$═C, 2H, dd); 4.82 (C1 anomeric H, 1H, d); 4.02 (═C—CH$_2$—O, 2H, d); 4.0-3.2 (—CH$_2$—CHOH—CH$_2$ and C2-6 sugar protons, 11H). One of the two C1 anomers crystallized from this clear oil upon adding acetone and cooling; m.p. 145-149° C. The $^1$H NMR of this anomer was identical to the above spectrum except for the C1 anomeric proton doublet which was shifted slightly to 4.79 ppm.

General Procedure C: Fluoroalkenyl Glycosides

In this procedure, an alkenyl glycoside is used as the starting material. The alkenyl content of an alkenyl glycoside mixture may be calculated based upon the known Flory distribution. For example, a Flory distribution of alkenyl polyglucoside such as that described in general procedure A would have an alkenyl content that could be calculated by the predicted Flory distribution of the alkenyl glycosides. The alkenyl content of the polyglycoside enriched mixture described in general procedure B can be estimated by calculating the alkenyl content predicted by the Flory distribution minus the alkenyl content of the monoglycoside portion which was removed in general procedure B. The alkenyl content of a monoglycoside sample could be calculated by standard means known to one skilled in the art.

Alkenyl glycoside powder (containing approximately 0.12 mole of alkenyl functionality based on the known Flory distribution of polyglycosides) is dissolved in water (200 mL) containing KHCO$_3$ (10 grams, 0.10 mole) and optionally Na$_2$SO$_3$ (126 mg, 1 mmole). The perfluoroalkyl iodide (0.10 mole) radical initiator (about 5 mmoles) and isopropyl alcohol (50 mL) are added. The two phase mixture is heated under nitrogen with vigorous stirring and held at reflux for 3 hours (78-82° C.). At the end of this time a clear, single phase solution forms. The reaction is cooled to ambient and 50% NaOH solution (8 g, 0.10 mole) is added. The reaction is again heated to 80° C. and held for 3 hours to complete dehydroiodination.

After cooling to ambient, the reaction solution is adjusted to pH 8 with hydrochloric acid; then diluted with water to give a solution containing approximately 30% (w/v) perfluoroalkyl polyglycoside actives.

Example 7

1-(2-(E/Z)-4,4,5,5,6,6,7,7,8,8,9,9,9-tridecafluoronon-2-enyloxy)-poly[1,6]glucoside (7)

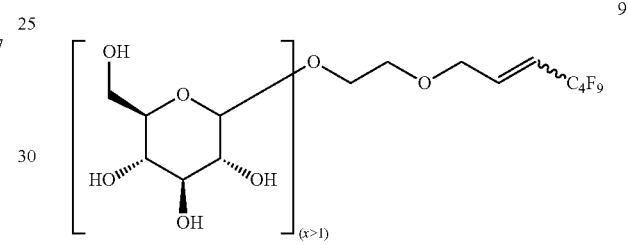

1-(2-(E/Z)-4,4,5,5,6,6,7,7,8,8,9,9,9-tridecafluoronon-2-enyloxy)-poly[1,6]glucoside was prepared according to general procedure C using perfluorohexyl iodide as the perfluoroalkyl iodide. A sample of this product was vacuum dried to a solid foam for NMR analysis. $^{19}$F NMR (CD$_3$OD): −82.8 (9CF$_3$—); −109.1/−113.0 (ratio 1/3, cis/trans isomers, α CF$_2$—); −123.0 (5CF$_2$—); −124.3 (6CF$_2$—); −124.7 (7CF$_2$—); −127.7 (8CF$_2$—). The occurrence of cis/trans isomers for the αCF$_2$— group indicates the point of attachment for the perfluoroalkyl group on the alkenyl polyglucoside is the double bond terminus.

Example 8

1-(2-(E/Z)-4,4,5,5,6,6,7,7,8,8,9,9,10,10,11,11,11-heptadecafluoroundec-2-enyloxy)-poly[1,6]glucoside (8)

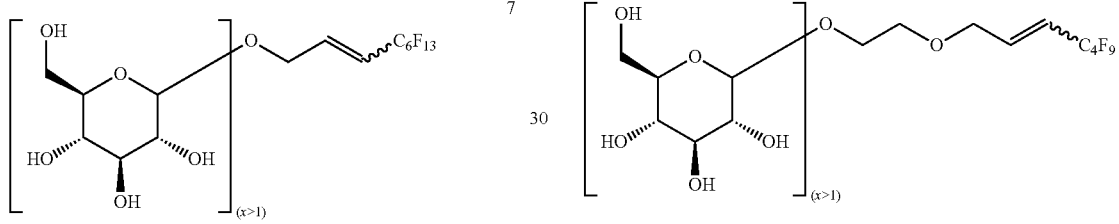

70 grams of allyl polyglucoside powder (containing approximately 0.12 mole of allyl functionality based on the known Flory distribution of polyglycosides) was dissolved in water (200 mL) containing KHCO$_3$ (10 grams, 0.10 mole) and (126 mg, 1 mmole) of Na$_2$SO$_3$. To this solution was added (55 g, 0.10 mole) of perfluorooctyl iodide followed by AIBN (0.82 g, 5 mmoles) dissolved in isopropyl alcohol (50 mL). The two phase mixture was heated under nitrogen with vigorous stirring and held at reflux for 3 hours (78-82° C.). At the end of this time a clear, single phase solution had formed. The reaction was cooled to ambient and 50% NaOH solution (8 g, 0.10 mole) was added. The reaction was again heated to 80° C. and held for 3 hours to complete dehydroiodination.

After cooling to ambient, the reaction solution was adjusted to pH 8 with hydrochloric acid; then diluted to a final volume of 330 mL with water to give a solution containing approximately 30% (w/v) perfluoroalkyl polyglycoside actives.

Example 9

1-(2-((E/Z)-4,4,5,5,6,6,7,7,7-nonafluorohept-2-enyloxy)ethoxy)poly[1,6]glucoside (9)

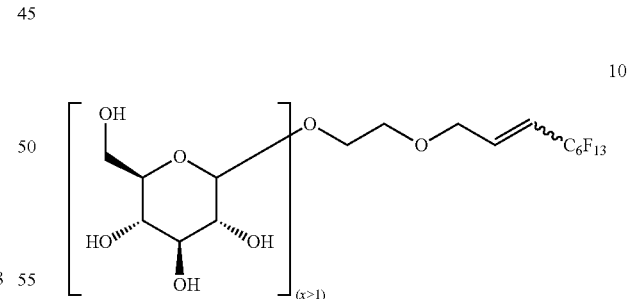

1-(2-((E/Z)-4,4,5,5,6,6,7,7,7-nonafluorohept-2-enyloxy)ethoxy)poly[1,6]glucoside was prepared according to general procedure C using perfluorobutyl iodide as the perfluoroalkyl iodide.

Example 10

1-(2-((E/Z)-4,4,5,5,6,6,7,7,8,8,9,9,9-tridecafluoronon-2-enyloxy)ethoxy)poly[1,6]glucoside (10)

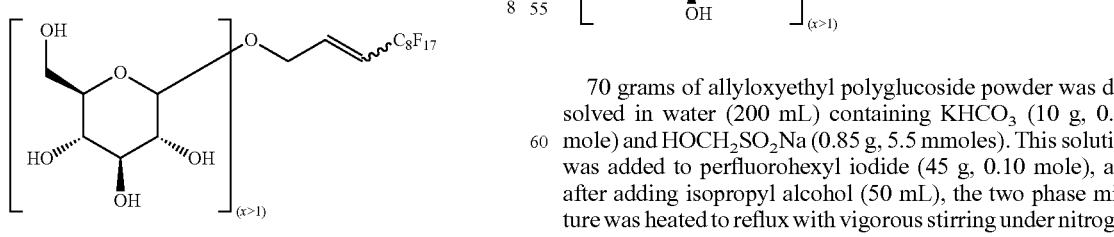

70 grams of allyloxyethyl polyglucoside powder was dissolved in water (200 mL) containing KHCO$_3$ (10 g, 0.10 mole) and HOCH$_2$SO$_2$Na (0.85 g, 5.5 mmoles). This solution was added to perfluorohexyl iodide (45 g, 0.10 mole), and after adding isopropyl alcohol (50 mL), the two phase mixture was heated to reflux with vigorous stirring under nitrogen (78-82° C.). After 3 hours a clear, dark solution had formed. This was cooled to ambient and 50% NaOH (8 g, 0.10 mole) added before heating again to 80° C. for 3 hours to complete dehydroiodination.

After cooling to ambient, the reaction solution was adjusted to pH 8 with HCl. Diluting with water to a final volume of 297 mL gave a clear solution containing about 30% (w/v) perfluoroalkyl polyglycoside actives. A vacuum dried sample of this product was analyzed by $^{19}$F NMR (CD$_3$OD): −82.8 (9CF$_3$—); −109.0/−113.0 (ratio 1/3, cis/trans isomers, αCF$_2$—); −123.0 (5CF$_2$—); −124.3 (6CF$_2$—); −124.9 (7CF$_2$—); −127.7 (8CF$_2$—). The occurrence of cis/trans isomers for the αCF$_2$— group indicates the point of attachment for the perfluoroalkyl group on the alkenyl polyglucoside is the double bond terminus.

Example 11

1-(2-((E/Z)-4,4,5,5,6,6,7,7,8,8,9,9,9-tridecafluoronon-2-enyloxy)ethoxy)glucoside (11)

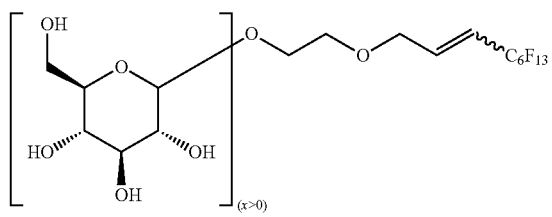

A Flory distribution of allyloxyethyl glucoside was prepared according to general procedure A. The product mixture from general procedure A and perfluorohexyl iodide was used in general procedure C to afford a Flory distribution of 1-(2-((E/Z)-4,4,5,5,6,6,7,7,8,8,9,9,9-tridecafluoronon-2-enyloxy)ethoxy)glucoside.

Example 12

1-(2-((E/Z)-4,4,5,5,6,6,7,7,9,9,9,10,10,11,11,11-pentadecafluoroundec-2-enyloxy)ethoxy poly[1,6]glucoside (12)

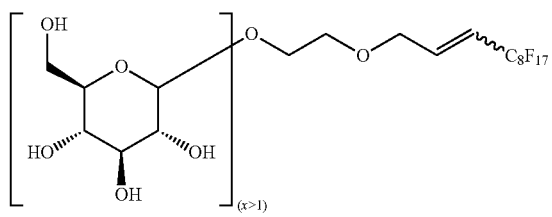

2-(2-((E/Z)-4,4,5,5,6,6,7,7,9,9,9,10,10,11,11,11-pentadecafluoroundec-2-enyloxy)ethoxy poly[1,6]glucoside was prepared according to general procedure C using perfluorooctyl iodide as the perfluoroalkyl iodide.

Example 13

1-(2-((E/Z)-4,4,5,5,6,6,7,7,8,8,9,9,10,10,11,11,11-heptadecafluoroundec-2-enyloxy)ethoxy glucoside (13)

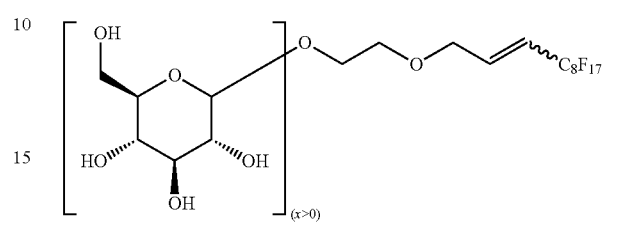

A Flory distribution of allyloxyethyl glucoside was prepared according to general A. The reaction product from general procedure A and perfluorooctyl iodide was used in general procedure C to afford a Flory distribution of 1-(2-((E/Z)-4,4,5,5,6,6,7,7,9,9,9,10,10,11,11,11-pentadecafluoroundec-2-enyloxy)ethoxy glucoside.

Example 14

1-(2-hydroxy-3-((E/Z)-4,4,5,5,6,6,7,7,8,8,9,9,9-tridecafluoronon-2-enyloxy)propoxy)poly[1,6]glucoside (14)

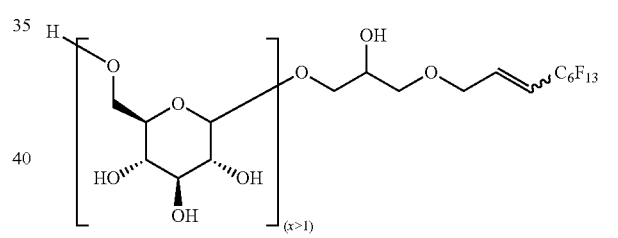

1-(2-hydroxy-3-((E/Z)-4,4,5,5,6,6,7,7,8,8,9,9,9-tridecafluoronon-2-enyloxy)propoxy)poly[1,6]glucoside was prepared according to general procedure C using perfluorohexyl iodide as the perfluoroalkyl iodide. A vacuum dried sample of this product was analyzed by $^{19}$F NMR (CD$_3$OD): −82.8 (9CF$_3$); −109.1/−113.0 (ratio 1/3, cis/trans isomers, αCF$_2$—); −123.0 (5CF$_2$—); −124.3 (6CF$_2$—); −124.9 (7CF$_2$—); −127.7 (8CF$_2$—).

Surface tension is a property that defines the spreading coefficient of one liquid over a second immiscible liquid. For a foamable solution, a positive spreading coefficient is indicative of a material that will spread over the fuel in question. During this process a very thin film is formed at the fuel/water interface. The formation of a film in conjunction with the foam generated during discharge, works to seal the fuel surface during the fir extinguishing process.

Foam expansion is measured by pouring a known volume of solution in to a blender. The solution is blended, and the mixture poured into a graduate cylinder. The foam volume is recorded and the foam expansion ratio is calculated by dividing foam volume by the initial volume before blending.

The time which passes between the time the blender has stopped and when the foam is converted to liquid is the drain time.

TABLE 1

Surface Tension & Foam Quality Data

| Ex. | L | n | $R^f$ | Surface Tension[a] (dynes/cm) | Foam Expansion[b] foam/liquid | 50% Drain Time[c] min:sec |
|---|---|---|---|---|---|---|
| 7 | bond | 0 | $C_6F_{13}$— | 17.3 | 2.9 | 2:41 |
| 8 | bond | 0 | $C_8F_{17}$— | 17.2 | 2.8 | 3:33 |
| 9 | —$CH_2CH_2O$— | 1 | $C_4F_9$— | 24.0 | 4.0 | 3:58 |
| 10 | —$CH_2CH_2O$— | 1 | $C_6F_{13}$— | 19.1 | 4.4 | 5:20 |
| 11[d] | —$CH_2CH_2O$— | 1 | $C_6F_{13}$— | 21.4 | 1.6 | <1:00 |
| 12 | —$CH_2CH_2O$— | 1 | $C_8F_{17}$— | 17.1 | 3.0 | 3:36 |
| 13[d] | —$CH_2CH_2O$— | 1 | $C_8F_{17}$— | na | no foam | na |
| 14 | —$CH_2CHOHCH_2O$— | 1 | $C_6F_{13}$— | 18.3 | 3.5 | 4:02 |

[a]Surface Tension in water measured at 1000 ppm concentration with a Kruss drop volume tensiometer.
[b]Foam volume/original solution volume at 1000 ppm concentration.
[c]Time required for foam to drain back to 50% of the original solution volume.
[d]Flory distribution of glycosides.

Examples 11 and 13 contain a Flory distribution of glycosides, including the monoglycoside. Both 11 and 13 gave poor drain time and foam expansion compared to examples 10 and 12, respectively. Examples 10 and 12 are enriched in the polyglycoside and were prepared by removal of the monoglycoside after formation of the alkenyl glycoside as described above. Comparison of the polyglycoside enriched examples (10 and 12) to the Flory distribution examples (11 and 13, respectively) shows that enrichment of the polyglycoside components affords desirable properties such as longer drain time, increased foam expansion, and decreased surface tension.

It is therefore intended that the foregoing detailed description be regarded as illustrative rather than limiting, and that it be understood that it is the following claims, including all equivalents, that are intended to define the spirit and scope of this invention.

The invention claimed is:

1. A fire extinguishing composition comprising:
a solvent; and
a first fluorosurfactant of formula (I)

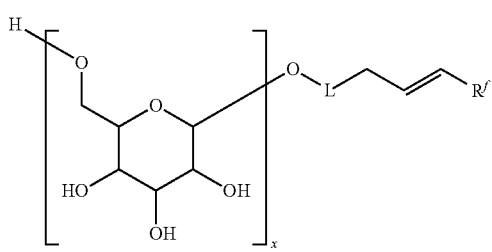
(I)

where
L is (—$CH_2CH_2O$—)$_n$, (—$CH_2CH(OH)CH_2O$—)$_n$, or (—$CH_2$—)$_n$;
n is 0 to 8;
x>1; and
$R^f$ is a fluorocarbon group.

2. The composition of claim 1, wherein $R^f$ is a $C_4$-$C_{10}$ fluorocarbon group; and wherein L is (—$CH_2CH_2O$—), (—$CH_2CH(OH)CH_2O$—), or —$CH_2$—.

3. The composition of claim 2, wherein $R^f$ is a $C_6$ fluorocarbon group.

4. The composition of claim 1, further comprising a hydrocarbon surfactant; and a second fluorosurfactant.

5. The composition of claim 1, wherein the solvent is selected from the group consisting of water, iso-propyl alcohol, t-butyl alcohol, glycol and butyl carbitol.

6. The composition of claim 1, wherein the first fluorosurfactant is of formula (II):

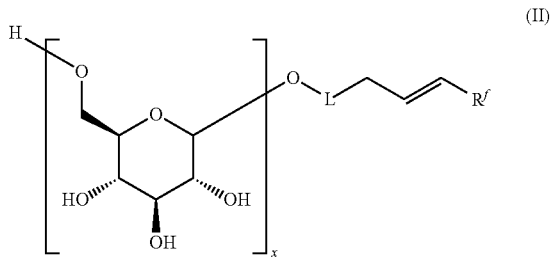
(II)

where
L is (—$CH_2CH_2O$—)$_n$, (—$CH_2CH(OH)CH_2O$—)$_n$, or (—$CH_2$—)$_n$;
n is 0 to 8;
x>1; and
$R^f$ is a fluorocarbon group.

7. The composition of claim 6, further comprising a hydrocarbon surfactant; and a second fluorosurfactant; and
wherein $R^f$ is a $C_4$-$C_{10}$ fluorocarbon group; and wherein L is (—$CH_2CH_2O$—), (—$CH_2CH(OH)CH_2O$—), or —$CH_2$—.

8. A method of extinguishing a fire comprising applying to said fire a composition comprising a solvent and a first fluorosurfactant of formula (I):

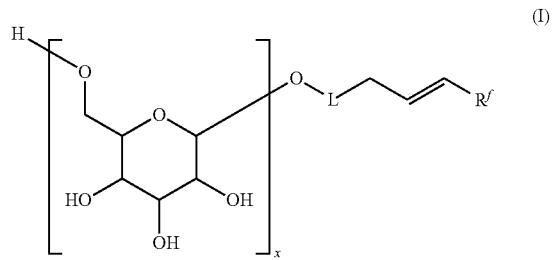
(I)

where
L is (—$CH_2CH_2O$—)$_n$, (—$CH_2CH(OH)CH_2O$—)$_n$, or (—$CH_2$—)$_n$;
n is 0 to 8;
x>1; and
$R^f$ a fluorocarbon group.

9. The method of claim 8, wherein $R^f$ is a $C_4$-$C_{10}$ fluorocarbon group; and wherein L is (—$CH_2CH_2O$—), (—$CH_2CH(OH)CH_2O$—), or —$CH_2$—.

10. The method of claim 8, wherein the composition further comprises a hydrocarbon surfactant; and a second fluorosurfactant.

11. The method of claim 8, wherein the first fluorosurfactant is of formula (II):

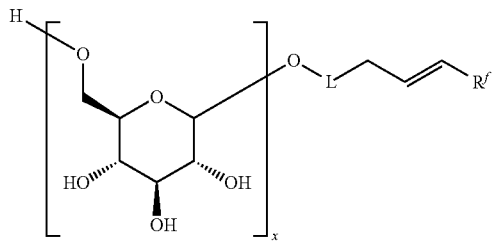

(II)

where

L is (—$CH_2CH_2O$—)$_n$, (—$CH_2CH(OH)CH_2O$—)$_n$, or (—$CH_2$—)$_n$;

n is 0 to 8;

x>1; and $R^f$ is a fluorocarbon group.

12. The method of claim 11, further comprising a hydrocarbon surfactant; and a second fluorosurfactant; and wherein $R^f$ is a $C_4$-$C_{10}$ fluorocarbon group; and wherein L is (—$CH_2CH_2O$—), (—$CH_2CH(OH)CH_2O$—), or —$CH_2$—.

13. A compound of formula (I):

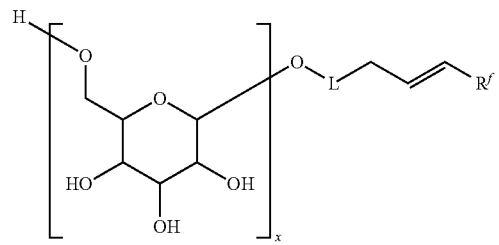

(I)

where

L is (—$CH_2CH_2O$—)$_n$, (—$CH_2CH(OH)CH_2O$—)$_n$, or (—$CH_2$—)$_n$;

n is 0 to 8;

x>1; and $R^f$ is hydrogen or a fluorocarbon group;

with the proviso that when $R^f$ is hydrogen, n is 1 to 8.

14. The compound of claim 13, where $R^f$ is a fluorocarbon group.

15. The compound of claim 14, wherein $R^f$ is a $C_4$-$C_{10}$ fluorocarbon group; and L is (—$CH_2CH_2O$—), (—$CH_2CH(OH)CH_2O$—), or —$CH_2$—.

16. The compound of claim 1, where $R^f$ is hydrogen and L is (—$CH_2CH_2O$—), (—$CH_2CH(OH)CH_2O$—), or —$CH_2$—.

17. The compound of claim 13, of formula (II):

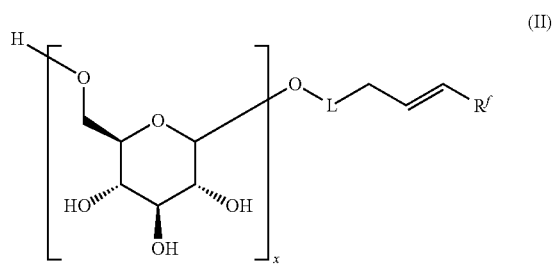

(II)

where

L is (—$CH_2CH_2O$—)$_n$, (—$CH_2CH(OH)CH_2O$—)$_n$, or (—$CH_2$—)$_n$;

n is 0 to 8;

x>1; and $R^f$ is hydrogen or a fluorocarbon group;

with the proviso that when $R^f$ is hydrogen, n is 1 to 8.

18. The compound of claim 17, where $R^f$ is a fluorocarbon group.

19. The compound of claim 18, where $R^f$ is a $C_4$-$C_{10}$ fluorocarbon group; and L is (—$CH_2CH_2$—), (—$CH_2CH(OH)CH_2O$—), or —$CH_2$—.

20. The compound of claim 17, where $R^f$ is hydrogen and L is (—$CH_2CH_2O$—), (—$CH_2CH(OH)CH_2O$—), or —$CH_2$—.

21. A fire extinguishing composition comprising:

a solvent; and a fluoroalkenyl glycoside surfactant having a non-Flory distribution of glycosides, and enriched in fluoroalkenyl poly[1,6]glycoside.

22. The composition of claim 21, wherein the fluoroalkenyl glycoside surfactant comprises at least 90 mole % fluoroalkenyl poly[1,6]glycoside and less than about 10 mole % fluoroalkenyl monoglycoside.

23. The composition of claim 22, wherein the fluoroalkenyl poly[1,6]glycoside is of formula (I):

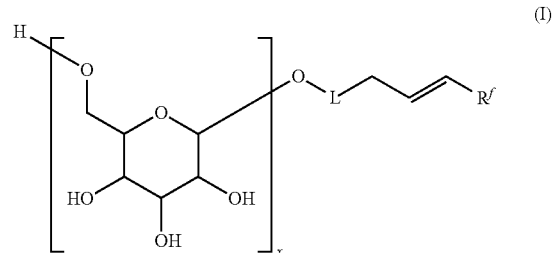

(I)

where

L is (—$CH_2CH_2O$—)$_n$, (—$CH_2CH(OH)CH_2O$—)$_n$, or (—$CH_2$—)$_n$;

n is 0 to 8;

x>1; and $R^f$ is a fluorocarbon group.

24. A fluoroalkenyl poly[1,6]glycoside surfactant made by the steps of:
- providing a sugar;
- providing an alkenyl alcohol;
- combining the sugar and the alkenyl alcohol to form an alkenyl glycoside mixture;
- removing alkenyl monoglycoside from the alkenyl glycoside mixture to form an alkenyl poly[1,6]glycoside;
- providing a fluoroalkylating agent;
- combining the alkenyl poly[1,6]glycoside and the fluoroalkylating agent in the presence of a radical initiator to form the fluoroalkenyl poly[1,6]glycoside.

* * * * *